United States Patent
Deng et al.

(10) Patent No.: US 10,321,689 B2
(45) Date of Patent: Jun. 18, 2019

(54) ANTIMICROBIAL TRADITIONAL CHINESE MEDICINE COMPOSITION, AND PREPARATION METHOD AND USE THEREOF

(71) Applicant: INFINITUS (CHINA) COMPANY LTD., Jiang Men, Guangdong (CN)

(72) Inventors: Wenjuan Deng, Guangdong (CN); Guangrong Liu, Guangdong (CN); Jian Tang, Guangdong (CN)

(73) Assignee: INFINITUS (CHINA) COMPANY LTD., Jiangmen, Guangdong (CN)

( * ) Notice: Subject to any disclaimer, the term of this patent is extended or adjusted under 35 U.S.C. 154(b) by 0 days.

(21) Appl. No.: 15/561,165

(22) PCT Filed: Jun. 24, 2016

(86) PCT No.: PCT/CN2016/087099
§ 371 (c)(1),
(2) Date: Sep. 25, 2017

(87) PCT Pub. No.: WO2017/036240
PCT Pub. Date: Mar. 9, 2017

(65) Prior Publication Data
US 2018/0116228 A1 May 3, 2018

(30) Foreign Application Priority Data

Aug. 28, 2015 (CN) .......................... 2015 1 0540235

(51) Int. Cl.
| | |
|---|---|
| *A61K 36/00* | (2006.01) |
| *A01N 65/22* | (2009.01) |
| *A61K 8/65* | (2006.01) |
| *A61K 8/73* | (2006.01) |
| *A61Q 19/00* | (2006.01) |
| *A61K 8/92* | (2006.01) |
| *A61K 8/97* | (2017.01) |
| *A01N 65/00* | (2009.01) |
| *C12P 1/00* | (2006.01) |

(52) U.S. Cl.
CPC ............. *A01N 65/22* (2013.01); *A01N 65/00* (2013.01); *A61K 8/65* (2013.01); *A61K 8/73* (2013.01); *A61K 8/92* (2013.01); *A61K 8/97* (2013.01); *A61Q 19/00* (2013.01); *C12P 1/00* (2013.01); *C12Y 301/01* (2013.01)

(58) Field of Classification Search
CPC ..................................................... A61K 36/00
See application file for complete search history.

(56) References Cited

U.S. PATENT DOCUMENTS 7,687,083 B2* 3/2010 Schempp ............. A61K 9/0014
424/725

FOREIGN PATENT DOCUMENTS

| CN | 1119113 A | 3/1996 |
|---|---|---|
| CN | 1280773 A | 1/2001 |
| CN | 1332968 A | 1/2002 |
| CN | 1947523 A | 4/2007 |
| CN | 103656302 A | 3/2014 |
| CN | 103830138 A | 6/2014 |
| CN | 105076246 A | 11/2015 |
| JP | H01290632 A | 11/1989 |
| JP | 2006022075 A | 1/2006 |
| JP | 2011079779 A | 4/2011 |

OTHER PUBLICATIONS

Xian, Anti-inflammatory effect of patchouli alcohol isolated from Pogostemonis Herba in LPS-stimulated RAW264.7 macrophages. Experimental and therapeutic medicine, (May 2011) vol. 2, No. 3, pp. 545-550 (Year: 2011).*
Yim, Anti-inflammatory and Immune-regulatory Effects of Subcutaneous Perillae Fructus Extract Injections on OVA-induced Asthma in Mice. Evidence-based complementary and alternative medicine : eCAM, (Mar. 2010) vol. 7, No. 1, pp. 79-86 (Year: 2010).*
International Search Report for PCT/CN2016/087099, dated Oct. 19, 2016, ISA/CN.
Lin, Yuan, Research Status of Usnea, China Pharmaceuticals, Oct. 30, 2011, pp. 84-86, vol. 20, No. 19, China Pharmaceuticals Bian Ji Bu, Chong Qing, China.
The European Search Report for application No. 16840669.2 dated Sep. 3, 2018 for an European counterpart application.
The 1st Office Action for application No. 2017-555745 dated Sep. 18, 2018 for a Japanese counterpart application.
Xian Yang et al: "Preliminary antibacterial evaluation of the chemical compositions in Herba pogostemonis oil", Pakistan Journal of Pharmaceutical Sciences, vol. 26, No. 6, Nov. 1, 2013 (Nov. 1, 2013), pp. 1173-1179.
Mahadik N et al: "Cardiovascular-protective, antioxidant and antimicrobial activities of a lichen species Usnea complanata",New Biotechnology, Elsevier BV, NL, vol. 25, Sep. 1, 2009 (Sep. 1, 2009), p. S8.

(Continued)

*Primary Examiner* — Qiuwen Mi
(74) *Attorney, Agent, or Firm* — Yue(Robert) Xu; Apex Attorneys at Law, LLP

(57) ABSTRACT

An antimicrobial traditional Chinese medicine composition, and a preparation method and a use thereof are provided, wherein the antimicrobial traditional Chinese medicine composition is made from raw materials comprising fructus perillae, patchouli and usnea. Through the reasonable matching application and synergistic effects of traditional Chinese medicines, the extracted composition has a broad-spectrum antimicrobial effect, and is suitable for being used as a natural preservative. Experiments show that for each microorganism of *Staphylococcus aureus, Escherichia coli, Pseudomonas aeruginosa, Candida albicans* and *Aspergillus niger* independently, the antimicrobial effect of the matched composition of the present invention is superior to the antimicrobial effect of single plants, the result where the total effect of the composition is better than sum of the effects of single plants is achieved, and the synergistic effect of antimicrobial effects among the plants is achieved.

9 Claims, No Drawings

6(56) References Cited

OTHER PUBLICATIONS

Yu-Cui Li et al: "Anti-Candida albicans activity and pharmacokinetics of pogostone isolated from Pogostemonis Herba", Phytomedicine, vol. 20, No. 1, Dec. 1, 2012 (Dec. 1, 2012), pp. 77-83.
Madamombe I. T. et al: "Evaluation of Antimicrobial Activity of Extracts From South African Usnea Barbata", Pharmaceutical Bio, Swets and Zeitlinger, Lisse, NL, vol. 41, No. 3, Jan. 1, 2003 (Jan. 1, 2003), pp. 199-202.

\* cited by examiner

ANTIMICROBIAL TRADITIONAL CHINESE MEDICINE COMPOSITION, AND PREPARATION METHOD AND USE THEREOF

CROSS-REFERENCE TO RELATED APPLICATION

The present application is a National Phase entry of PCT Application No. PCT/CN2016/087099, titled "ANTIMICROBIAL TRADITIONAL CHINESE MEDICINE COMPOSITION, PREPARATION METHOD AND USE THEREOF", filed Jun. 24, 2016, which claims the priority of Chinese Patent Application No. 201510540235.4, as filed on Aug. 28, 2015 and titled with "ANTIMICROBIAL TRADITIONAL CHINESE MEDICINE COMPOSITION, PREPARATION METHOD AND USE THEREOF", and the disclosures of both of which are incorporated herein by reference.

FIELD

The present invention relates to the field of traditional Chinese medicine, particularly to an antimicrobial traditional Chinese medicine composition, preparation method and use thereof.

BACKGROUND

Generally, the term "antimicrobial" refers to sterilization, bacteriostasis, anti-mildew, anticorrosion and the like. Antimicrobial agents or preservatives are the materials that can inhibit the growth of microorganism. In daily life, cosmetics are contaminated by microorganism and easily lead to deterioration. Under normal circumstances, this can be reflected on the external appearance. For example, moulds and yeasts usually cause the mildew spots on edges of the packages; turbidity, precipitation, color change, pH change, foaming and change of taste may appear in products contaminated by microorganism; if the products are emulsified bodies, demulsification, pieces and so on may appear. Adding preservatives to cosmetics is to protect the products from the contamination of microorganism. If the amount of preservative added is not enough, there may be microbial adaptation to the surrounding growth environment, resulting in drug resistance, resulting in anti-corrosion failure.

At present, the common preservatives used in cosmetics include hydantoin (DMDMH), Kathon series, bronopol, butyl-carbamic acid 3-iodo-2-propynyl ester (IPBC), Nipagin esters, Triclosan, etc. However, these preservatives have their limitations: for example, DMDMH releases methanol during use and causes potential safety risk; Kathon series contain chlorine and may cause irritation to some skin types; use of bronopol easily generates nitrite amine which is a carcinogen; IPBC may cause the user to overdose iodine; Nipagin esters are accumulated in the adipose tissue easily. In addition, p-hydroxybenzoic acid preservatives have been shown to demonstrate a certain ability to mimic female estrogen in a particular test system, adversely affecting human safety and physiological systems. Triclosan has been shown to have a negative impact on the environment. Therefore, a low toxicity, high efficiency, pollution-free, natural preservative is needed urgently in the market.

In recent years, under the hot-wave of return to nature and enjoying green and health, adding pure natural preservatives to cosmetics becomes a hot spot of promotion and development at home and abroad. Extracting natural antimicrobial agents, which are strong and wide efficiency, safe and non-toxic, from raw materials becomes an important development direction in the future.

SUMMARY

In view of the above, the object of the present invention is to provide an antimicrobial traditional Chinese medicine composition, preparation method and use thereof. The antimicrobial traditional Chinese medicine composition provided in this invention has a broad spectrum antimicrobial activity, and it is natural and mild.

An antimicrobial traditional Chinese medicine composition provided in the present invention is made from materials comprising Perillae Fructus, Pogostemonis Herba and Usnea.

Preferably, in parts by weight, said materials comprise 60-80 parts of Perillae Fructus, 10-20 parts of Pogostemonis Herba and A parts of Usnea, $0 < A \leq 20$.

Preferably, in parts by weight, said materials comprise 60 parts of Perillae Fructus, 20 parts of Pogostemonis Herba and 20 parts of Usnea.

Preferably, in parts by weight, said materials comprise 80 parts of Perillae Fructus, 10 parts of Pogostemonis Herba and 10 parts of Usnea.

Preferably, in parts by weight, said materials comprise 70 parts of Perillae Fructus, 15 parts of Pogostemonis Herba and 15 parts of Usnea.

A method for preparing the antimicrobial traditional Chinese medicine composition is also provided in the present invention, comprising the following steps: Perillae Fructus, Pogostemonis Herba and Usnea are mixed; ethanol percolation extraction is performed to obtain the antimicrobial traditional Chinese medicine composition.

Preferably, after mix and before extraction, the method also comprises enzymolysis using lipases.

More preferably, enzymolysis is performed at 40° C.-60° C. for 1 h-2 h using a lipase which has an activity of 5 U/g-10 U/g.

Preferably, in detail, said mix is: mixing Perillae Fructus, Pogostemonis Herba and Usnea; adding water and grinding until 60-200 mesh; adjusting pH to 4-7.

Preferably, said extraction time is 24 h-30 h.

After extraction, the method also comprises: filtering and collecting filtered solution; said filtered solution is subjected to concentration, constant volume and aging, successively, to obtain the antimicrobial traditional Chinese medicine composition.

Compared to prior art, the antimicrobial traditional Chinese medicine composition provided in the present invention is made from Perillae Fructus, Pogostemonis Herba and Usnea. Through the reasonable compatibility and synergistic effect of the traditional Chinese medicine, so that the extracted composition has a broad spectrum antimicrobial activity and is suitable for using as natural preservative. Experiments demonstrated that said composition has a better antimicrobial effect than single plant against each of *Staphylococcus aureus, Escherichia coli, Pseudomonas aeruginosa, Candida albicans* and *Aspergillus niger*. This achieves a result of 1+1 greater than 2, reflecting the synergistic effect in antibacterial effects between plants.

The application also provides use of the above-mentioned antimicrobial traditional Chinese medicine composition as a preservative for pharmaceuticals, cosmetics or foods.

The examples of the present invention apply the above antimicrobial traditional Chinese medicine compositions to cosmetics and carry out anti-corrosion challenge experiments. The results show that the cosmetic samples are excellent in the anticorrosive challenges of *Staphylococcus aureus, Escherichia coli, Pseudomonas aeruginosa, Candida albicans* and *Aspergillus niger.*

DETAILED DESCRIPTION OF THE INVENTION

The present invention disclosed an antimicrobial traditional Chinese medicine composition, preparation method and use thereof. One of ordinary skill in the art can use this disclosure for reference and improve the technological parameter to reach the same. In particular, it is pointed out that all similar replacements and changes are obvious for one of ordinary skill in the art, so they will be considered within the scope of the present invention. The methods and applications of the present invention have been described by way of preferred embodiments, and it will be apparent to those of ordinary skill in the art that changes and combinations of the methods and applications described herein can be made without departing from the content, spirit and scope of the present invention to implement and apply the techniques of the present invention An antimicrobial traditional Chinese medicine composition provided in the present invention is made from materials comprising Perillae Fructus, Pogostemonis Herba and Usnea In the present invention, said materials comprise Perillae Fructus. It is recorded in «Chinese Pharmacopoeia» that the nature of Perillae Fructus is mild and its taste is spicy; it returns to lung. It has functions for clearing away phlegm, relieving asthma and moistening the intestines.

In the present invention, said materials comprise Pogostemonis Herba. It was recorded in «Chinese Pharmacopoeia» that Pogostemonis Herba is the dry above-ground portion of Pogostemon cablin (Blanco) Benth. which belongs to Labiatae family. According to records of «Chinese Materia Medica», in pharmacological effects, pogostone has significant inhibitory effect on *Candida albicans, Cryptococcus neoformans, Rhizopus nigricans* and other fungi in vitro; it has certain inhibitory effect on alpha hemolytic *streptococcus* and other bacteria; fresh juice from the leaves of Pogostemon cablin (Blanco) Benth. has certain inhibitory effect on the growth of *Staphylococcus aureus, Staphylococcus albus,* and *Bacillus subtilis*; pogostone can inhibit the growth of mould such as *Penicillium* and can be used as a preservative for oral liquid.

In the present invention, said materials comprise Usnea (Scientific name: *Usnea diffracta* Vain.) which belongs to Lichenes, Usneaceae family. It grows on the old tree branches and alpine rocks in the mountains, hanging from the top with a filamentous shape. It was recorded in «Chinese Materia Medica» that Usneaceae family and other lichens contain antimicrobial substances, especially usnic acid which has a prominent antimicrobial effect. Experiments in test tubes showed that usnic acid has a strong inhibitory effect on *Pneumococcus*, hemolytic *streptococcus*, diphtheria *bacillus, Mycobacterium tuberculosis*; it has a weaker inhibitory effect on *Staphylococcus aureus* compared to bacteria mentioned above, but still better than the inhibitory effect on Gram-negative bacteria.

The present invention is based on a formula mainly comprising Perillae Fructus, Pogostemonis Herba and Usnea. The antimicrobial traditional Chinese medicine composition in this invention has a broad spectrum antimicrobial activity, better than that of the single herb, which overcomes the strain limitation of single herb, therefore showing a significant bacteriostasis effect.

In preferred embodiments of the present invention, in parts by weight, said materials comprise 60-80 parts of Perillae Fructus, 10-20 parts of Pogostemonis Herba and A parts of Usnea, $0<A\leq 20$. The preferred proportions of the three Chinese herbs of the present invention can maximize the inhibition of bacterial growth.

In one embodiment of the present invention, in parts by weight, said materials comprise 60 parts of Perillae Fructus, 20 parts of Pogostemonis Herba and 20 parts of Usnea. In another embodiment of the present invention, in parts by weight, said materials comprise 80 parts of Perillae Fructus, 10 parts of Pogostemonis Herba and 10 parts of Usnea. In another embodiment of the present invention, in parts by weight, said materials comprise 70 parts of Perillae Fructus, 15 parts of Pogostemonis Herba and 15 parts of Usnea.

A method for preparing the antimicrobial traditional Chinese medicine composition is also provided in the present invention, comprising the following steps: Perillae Fructus, Pogostemonis Herba and Usnea were mixed; ethanol percolation extraction was performed to obtain the antimicrobial traditional Chinese medicine composition.

The technical solution of the embodiment in the present invention can overcome the problems in traditional processes for traditional Chinese medicine extraction, such as heavy odor of the traditional Chinese medicine extract, low yield of active ingredients, large amount of impurities, narrow antimicrobial spectrum and strong irritations.

In embodiments of the present invention, an antimicrobial traditional Chinese medicine composition was obtained by mixing Perillae Fructus, Pogostemonis Herba and Usnea then extracting the composition by ethanol percolation.

In the present invention, the content of said Perillae Fructus, Pogostemonis Herba and Usnea are the same as those described above and will not be repeated here. Preferably, Perillae Fructus, Pogostemonis Herba and Usnea were crushed separately and their powders were mixed together. Preferably, said mix is: mixing Perillae Fructus, Pogostemonis Herba and Usnea; adding water and grinding until 60-200 mesh; adjusting pH to 4-7. In the present invention, said "crush", "grind" and the like are well-known technologies for those of ordinary skill in the art. In one embodiment of this invention, the pH of grinded materials can be adjusted to pH 5-6, preferably 5.

In embodiments of the present invention, the antimicrobial traditional Chinese medicine composition was obtained by ethanol percolation extraction after the adjustment of pH. Preferably, before ethanol percolation extraction, lipases were added for enzymolysis in the present invention, reducing the irritation significantly.

Preferably, after mix and before extraction, embodiments of the present invention also comprise: enzymolysis at 40° C.-60° C. for 1 h-2 h using a lipase which has an activity of 5 U/g-10 U/g. In the present invention, said lipase is commercially available in the market; preferably, it has an enzyme activity of 5 U/g-10 U/g. Said enzymolysis was commonly used in the field; preferred temperature was 45° C.-55° C.

In embodiments of the present invention, the antimicrobial traditional Chinese medicine composition was obtained by adding ethanol for ethanol percolation extraction. In the present invention, said ethanol percolation is: using ethanol as a solvent; placing moderately crushed materials into percolator; adding ethanol from the top constantly; extracting medicinal ingredients from materials in the course of flowing the solvent through the drug layers. The present invention adopted the percolation method to reduce the lost of volatile matter.

In embodiments of the present invention, 80 wt %-95 wt % ethanol solution can be used as an extraction solvent. In one embodiment of the present invention, concentration of said ethanol solution was 80 wt %-95 wt %; the mass ratio of said ethanol solution to (herb) materials mentioned above was (2000-3000):100, preferably. Preferred extraction time was 24 h-30 h; in one embodiment of the present invention, percolation extraction time was 24 h.

Preferably, after extraction, the present invention also comprised: filtering and collecting filtered solution; said filtered solution was subjected to concentration, constant volume and aging, successively, to obtain the antimicrobial traditional Chinese medicine composition.

There is no limitation for said filter method in the present invention, any common filtrations in the field can be used here. In embodiments of the present invention, filtered solution after filtration was concentrated under conditions such as low temperature and reduced pressure to remove solvent; then solvent was replaced by dipropylene glycol or caprylic/capric glycerides or other oils, polyols; solution volume was adjusted to constant volume. Herein, said low temperature and reduced pressure concentration is well-known technologies for those of ordinary skill in the art; preferably, temperature was lower than 100° C., more preferably lower or equal to 50° C.; reduced pressure refers to negative pressure by evacuation, usually less than 0 Pa, for example, −0.02 MPa. In embodiments of the present invention, final constant volume can be 1 to 5 folds of the mass of the raw materials mentioned above.

In embodiments of the present invention, after constant volume reached certain amount, aging was carried out; filtration was performed after stratification; supernatant was collected to obtain the natural preservative extract, i.e. said antimicrobial traditional Chinese medicine composition in the present invention. Herein, preferred temperature of said aging was −5° C.-−10° C.; preferred aging time was 10 h-20 h, more preferably 12 h-15 h. In the present invention, percolation method was used to reduce the lost of volatile matter and aging was used to remove some impurities, therefore small molecules can be retained better to obtain the antimicrobial traditional Chinese medicine composition.

In the present invention, bacteriostasis tests were performed after having the antimicrobial traditional Chinese medicine composition. Results showed that the technologic solution provided in the present invention ensured the broad spectrum antimicrobial activity effect of said composition while attenuating the color of the composition. The product was stable and suitable for using as a preservative for cosmetics and the like.

The present invention also provides applications of said antimicrobial traditional Chinese medicine composition in above technical solution as a preservative for pharmaceuticals, cosmetics or foods.

In the field of pharmaceuticals, cosmetics or foods, said antimicrobial traditional Chinese medicine composition as a preservative, has anticorrosion and antibacterial effects. Herein, type of microorganism was one or more of *Staphylococcus aureus, Escherichia coli, Pseudomonas aeruginosa, Candida albicans* and *Aspergillus niger*. The pharmaceutical to which the present invention was applied is usually a topical skin medicine and a cosmetic such as a cosmetic for daily use. However, the application of the antimicrobial traditional Chinese composition prepared by the present invention is not limited thereto.

A cosmetic provided in the present invention comprises said antimicrobial traditional Chinese medicine composition. Adding said antimicrobial traditional Chinese medicine composition to cosmetics can effectively inhibit the growth of microorganism in cosmetics, extending the shelf life of the cosmetics, ensuring the safety of the product, avoiding the potential infection caused by the contaminated product in customers.

In embodiments of the present invention, said cosmetics comprise: aqueous components, oily components, said antimicrobial traditional Chinese medicine composition and functional components. Herein, preferably, said aqueous components include water, glycerol, complexing agent and water-soluble emulsifier; said oily components include vegetable oils, C16-18 alcohols and oil-in-water emulsifier. In the present invention, said functional components include but not limit to anti-wrinkle component, hydrating component and brightening component. In one embodiment of the present invention, said functional components include collagen and oat-β-glucan.

In the preferred embodiments of the present invention, said cosmetics comprise water, glycerol, complexing agent, water-soluble emulsifier, vegetable oils, C16-18 alcohols, oil-in-water emulsifier, the above antimicrobial traditional Chinese medicine composition and functional components.

Herein, by mass fraction, said cosmetics preferably comprise 4%-10% glycerol, more preferably 5% glycerol. Said cosmetics preferably comprise 0.01%-0.05% complexing agent, such as ethylenediaminetetraacetic acid disodium salt. Said cosmetics preferably comprise 0.1%-0.5% water-soluble emulsifier, such as acryloyl dimethyl taurine/vinyl pyrrolidone (VP) copolymer, which can be referred to as AVC.

By mass fraction, said cosmetics preferably comprise 5%-10% vegetable oils, more preferably 8% vegetable oils. In one embodiment of the present invention, said vegetable oil was *camellia* seed oil. Said cosmetics preferably comprise 1%-5% C16-18 alcohols, more preferably 2%-4% C16-18 alcohols. Said cosmetics preferably comprise 1%-2% oil-in-water emulsifier, such as A-165 emulsifier.

In the present invention, by mass fraction, said cosmetics preferably comprise 0.5%-1% said antimicrobial traditional Chinese medicine composition. Said cosmetics preferably comprise 5%-10% functional components. In one embodiment of the present invention, said cosmetics comprise 2% collagen and 5% oat-β-glucan, which have anti-wrinkle function and so on. In embodiments of the present invention, the amount of water used was to make up the total mass fraction as 100%.

The method for preparing the cosmetic was not particularly limited in the present invention, and is preferably carried out according to the following method:

1) water, glycerol and complexing agent are mixed and heated; water-soluble emulsifier is added to obtain aqueous phase;
2) oil-in-water emulsifier, C16-18 alcohols and vegetable oils are mixed and heated to obtain oil phase:
3) said oil phase is added to aqueous phase and homogenized; said antimicrobial traditional Chinese medicine composition, collagen and oat-β-glucan are added to obtain the product.

In the method described above, when preparing aqueous phase, preferably, said heating was preferably to temperature 80° C.-90° C. and under stirring at a speed of 3000 rpm/min. When preparing oil phase, said heating was preferably to temperature 80° C.-90° C. and under stirring at a speed of 300 rpm/min.

In the present invention, said homogenization is well-known technologies for those of ordinary skill in the art. Preferably, said homogenization speed is 500 rpm/min and homogenization time is 5 min. Preferably, after homogenization in embodiments of the present invention, temperature was reduced to 40° C.-50° C. with stirring. The above antimicrobial traditional Chinese compositions and functional components are added to the examples of the present invention, preferably under stirring conditions. The stirring speed can be 500 rpm/min; temperature was further reduced to room temperature to obtain the cosmetic.

After obtaining the cosmetics, anti-corrosion challenge experiments were carried out. The results show that said cosmetic was excellent in the anticorrosive challenge of *Staphylococcus aureus, Escherichia coli, Pseudomonas aeruginosa, Candida albicans* and *Aspergillus niger*.

For a further understanding of the present invention, the antimicrobial Chinese medicine composition, preparation method and use thereof provided in the present invention are described in detail below in connection with the examples.

In the following examples, lipase used was food grade and purchased from Zhengzhou Ruijia Food Additives Co. Ltd.; *camellia* seed oil (material name: Dongbaek (Tsubaki) oil) was purchased from BIOSPECTRUM (Korea); C16-18 alcohols was purchased from Kening Chemical Co. Ltd. (China), product model: Lanette MY; collagen was purchased from Wuhan Biocar Biopharmaceuticals Co. Ltd.; oat-β-glucan was purchased from Beijing Hua Xia Zhong Fang Biological Technology Co., Ltd.

EXAMPLE 1

60 g Perillae Fructus, 20 g Pogostemonis Herba and 20 g Usnea were crushed separately and then mixed well; 100 g water was added and the materials were grinded until a size of 60-200 mesh. pH of the system was adjusted to 5. Lipase was added until enzyme activity reached 10 U/g and enzymolysis was performed at 40° C. for 2 h. 2000 g 80 wt % ethanol solution was added for percolation extraction which was carried out for 24 h. Filtration was performed and filtered solution was collected. Solvent was removed by concentration under low temperature and reduced pressure conditions and replaced by caprylic capric triglyceride, giving a constant volume of 200 g. Aging was carried out at −10° C. for 12 h; filtration was performed after stratification; supernatant was collected to obtain the natural preservative extract (antimicrobial traditional Chinese medicine composition).

EXAMPLE 2

80 g Perillae Fructus, 10 g Pogostemonis Herba and 10 g Usnea were crushed separately and then mixed well; 100 g water was added and the materials were grinded until a size of 60-200 mesh. pH of the system was adjusted to 5. Lipase was added until enzyme activity reached 5 U/g and enzymolysis was performed at 60° C. for 1 h. 3000 g 95 wt % ethanol solution was added for percolation extraction which was carried out for 24 h. Filtration was performed and filtered solution was collected. Solvent was removed by concentration under low temperature and reduced pressure conditions and replaced by caprylic capric triglyceride, giving a constant volume of 200 g. Aging was carried out at −10° C. for 12 h; filtration was performed after stratification; supernatant was collected to obtain the natural preservative extract (antimicrobial traditional Chinese medicine composition).

EXAMPLE 3

70 g Perillae Fructus, 15 g Pogostemonis Herba and 15 g Usnea were crushed separately and then mixed well; 100 g water was added and the materials were grinded until a size of 60-200 mesh. pH of the system was adjusted to 5. Lipase was added until enzyme activity reached 5 U/g and enzymolysis was performed at 60° C. for 1 h. 3000 g 95 wt % ethanol solution was added for percolation extraction which was carried out for 24 h. Filtration was performed and filtered solution was collected. Solvent was removed by concentration under low temperature and reduced pressure conditions and replaced by caprylic capric triglyceride, giving a constant volume of 200 g. Aging was carried out at −10° C. for 12 h; filtration was performed after stratification; supernatant was collected to obtain the natural preservative extract (antimicrobial traditional Chinese medicine composition).

COMPARATIVE EXAMPLE 1

(1) 100 g Perillae Fructus was crushed. 3000 g 95 wt % ethanol solution was added for percolation extraction.
(2) Percolation extraction was carried out for 24 h. Filtration was performed and filtered solution was collected.
(3) Solvent was removed by concentration under low temperature and reduced pressure conditions and replaced by caprylic capric triglyceride, giving a constant volume of 200 g.
(4) Aging was carried out at −10° C. for 12 h; filtration was performed after stratification; supernatant was collected to obtain Perillae Fructus extract.

COMPARATIVE EXAMPLE 2

(1) 100 g Pogostemonis Herba was crushed. 3000 g 95 wt % ethanol solution was added for percolation extraction.
(2) Percolation extraction was carried out for 24 h. Filtration was performed and filtered solution was collected.
(3) Solvent was removed by concentration under low temperature and reduced pressure conditions and replaced by caprylic capric triglyceride, giving a constant volume of 200 g.
(4) Aging was carried out at −10° C. for 12 h; filtration was performed after stratification; supernatant was collected to obtain Pogostemonis Herba extract.

COMPARATIVE EXAMPLE 3

(1) 100 g Usnea was crushed. 3000 g 95 wt % ethanol solution was added for percolation extraction.
(2) Percolation extraction was carried out for 24 h. Filtration was performed and filtered solution was collected.
(3) Solvent was removed by concentration under low temperature and reduced pressure conditions and replaced by caprylic capric triglyceride, giving a constant volume of 200 g.
(4) Aging was carried out at −10° C. for 12 h; filtration was performed after stratification; supernatant was collected to obtain Usnea extract.

EXAMPLE 4

(1) 80 g Perillae Fructus, 10 g Pogostemonis Herba and 10 g Usnea were crushed separately and then mixed well. 3000 g 95 wt % ethanol solution was added for percolation extraction.

(2) Percolation extraction was carried out for 24 h. Filtration was performed and filtered solution was collected.

(3) Solvent was removed by concentration under low temperature and reduced pressure conditions and replaced by caprylic capric triglyceride, giving a constant volume of 200 g.

(4) Aging was carried out at −10° C. for 12 h; filtration was performed after stratification; supernatant was collected to obtain the natural preservative extract (antimicrobial traditional Chinese medicine composition).

EXAMPLE 5

Bacteriostasis Test

1. Test Strains

*Staphylococcus aureus* (ATCC 8739), *Escherichia coli* (ATCC 6538), *Pseudomonas aeruginosa* (ATCC 9027), *Candida albicans* (ATCC 10231), *Aspergillus niger* (ATCC 16404).

2. Culture Medium

TSB solid medium: peptone 10 g/L, NaCl 10 g/L, $K_2HPO_4$ 2.5 g/L, yeast extract 3 g/L, agar 15 g/L, were dissolved in distilled water, adjusted to pH 7.2±0.2, autoclaved at 115° C. for 20 min. TSB liquid medium: peptone 10 g/L, NaCl 10 g/L, $K_2HPO_4$ 2.5 g/L, yeast extract 3 g/L, were dissolved in distilled water, adjusted to pH 7.2±0.2, autoclaved at 115° C. for 20 min.

SDB solid medium: peptone 10 g/L, glucose 20 g/L, $K_2HPO_4$ 3 g/L, yeast extract 5 g/L, agar 15 g/L, were dissolved in distilled water, autoclaved at 115° C. for 20 min. SDB liquid medium: peptone 10 g/L, glucose 20 g/L, $K_2HPO_4$ 3 g/L, yeast extract 5 g/L, were dissolved in distilled water, autoclaved at 115° C. for 20 min.

3. Bacterial Suspension Preparation and Inoculation

100 µL glycerin preserved *Staphylococcus aureus, Escherichia coli, Pseudomonas aeruginosa* were spreaded on TSB solid medium and cultured at cultured at 37° C. for 2 days. The suspension was resuspended with physiological saline to obtain a bacterial suspension and counted by plate culture. The concentration of test bacteria was adjusted to $10^5$-$10^6$ CFU/mL.

100 µL *Candida albicans* and *Aspergillus niger* were spreaded on SDB solid medium and cultured at cultured at 30° C. for 2 days. The suspension was resuspended with physiological saline to obtain a bacterial suspension and counted by plate culture. The concentration of test bacteria was adjusted to $10^5$-$10^6$ CFU/mL.

4. Sample Bacteriostasis Test 4.1 Cylinder Plate Method

TSB or SDB solid medium was poured into a culture dish. After coagulation, 100 µL of the test bacteria was uniformly coated on the culture medium. Two sterile Oxford cups [inner diameter (6.0±0.1) mm, outer diameter (8.0±0.1) mm and high (10.0±0.1) mm] were placed equidistantly on the medium. 200 µL sample to be tested was injected into the cup; physiological saline or saline containing 50 µL DMSO (dimethyl sulfoxide) was served as control. After incubation in incubator at 37° C. or 30° C. for 2 days, the diameters of the inhibition zone of drugs were measured with a ruler and averages were taken.

4.2 Microplate Method

100 µL samples (initial concentration) were added to the microwells and 100 µL of 2×TSB or 2×SDB liquid medium containing the test bacteria concentration of $1 \times 10^5$ CFU/mL was added and mixed to prepare the test sample, i.e. test concentration of test sample was 50 wt % of the initial concentration. After incubation in incubator at 37° C. or 30° C. for 2 days, bacteria growth was observed. The premise of result determination was that growth control was good and there was clearly no bacteria growth in blank control.

5. Minimum Inhibitory Concentration (MIC) Test 5.1 To test the MIC of *Staphylococcus aureus, Escherichia coli, Pseudomonas aeruginosa*, follow the method:

(1) Sample preparation Test samples were diluted with saline to test concentration.

(2) Bacterial suspension preparation Bacterial suspension was diluted with 2×TSB or 2×SDB liquid medium to a final bacteria concentration of $10^5$ CFU/mL.

(3) Culture and result reading-out 100 µL bacterial suspension and 100 µL drug sample were added to the microwells. A negative control without bacteria and a normal growth control without drug were applied. Each drug has three parallel and the average was taken. The microplate was incubated at 37° C. or 30° C. in a wet box and observed after 48 h using direct method to read data. The premise of result determination was: growth control was good, there was clearly no bacteria growth in blank control and the growth of bacteria in other wells was inhibited with the increase of drug concentration gradient.

5.2 MIC of *Aspergillus niger* Test

Cylinder plate method was applied. SDB solid medium was poured into a culture dish. After coagulation, 100 µL *Aspergillus niger* ($10^5$ CFU/mL) was uniformly coated on the culture medium. Three sterile Oxford cups [inner diameter (6.0±0.1) mm, outer diameter (8.0±0.1) mm and high (10.0±0.1) mm] were placed equidistantly on the medium. 200 µL samples (diluted by saline) with different concentration were injected into the cup. A normal growth control without drug and saline were served as controls. The premise of result determination was: the growth of bacteria was good in normal growth control and saline control and the growth of bacteria in other wells was inhibited with the increase of drug concentration gradient.

Compared with single traditional Chinese medicine, bacteriostasis effects of the product in the present invention were shown in Table 1. Table 1 was the MIC values of Examples 1 to 4 and Comparative Examples 1 to 3.

TABLE 1

MIC values of Examples 1 to 4 and Comparative Examples 1 to 3.

| Strains | MIC value (μL/mL) | | | | | | |
|---|---|---|---|---|---|---|---|
| | Example 1 | Example 2 | Example 3 | Comparative Example 1 | Comparative Example 2 | Comparative Example 3 | Example 4 |
| Staphylococcus aureus | 0.6125 | 0.65 | 0.63 | 12 | 0.2025 | 10 | 0.1025 |
| Escherichia coli | 2.25 | 2.2 | 2.3 | 2.15 | — | — | 2.15 |
| Pseudomonas aeruginosa | 3.5 | 3.8 | 3.7 | 100 | — | — | 3.8 |
| Candida albicans | 5.25 | 5.13 | 5.03 | — | — | 80 | 5.15 |
| Aspergillus niger | 1.5 | 1.125 | 1.25 | 1.75 | 6.25 | — | 1.2 |

Table 1 showed that within a concentration of 100 μL/mL, Perillae Fructus has no antibacterial effect against *Candida albicans*, and the antibacterial effect on *Pseudomonas aeruginosa* was weak, and the antibacterial effect on *Staphylococcus aureus* was at general level. Within a concentration of 100 μL/mL, Pogostemonis Herba has no antibacterial effect on *Escherichia coli, Pseudomonas aeruginosa* and *Candida albicans*. Within a concentration of 100 μL/mL, Usnea has no antibacterial effect on *Escherichia coli, Pseudomonas aeruginosa* and *Aspergillus niger*, and the antibacterial effect on *Staphylococcus aureus* was at general level, and antibacterial effect on *Candida albicans* was weak.

It can be seen that, first, the present invention achieves broad spectrum antimicrobial effect by reasonable compatibility between plants. Second, for each strain alone, the antibacterial effect of the composition after compatibility is superior to that of single plant, achieving a result of 1+1 greater than 2, reflecting the synergistic effect of antibacterial effects between plants.

The antibacterial effect of the composition of the present invention is remarkable, and has broad spectrum antibacterial effect which is better than that of the single herb. It overcomes the limitation of the single herb to certain strains, and is suitable for use as a natural preservative. At the same time, the ratio of the three Chinese herbs of the present invention can maximize the inhibition of bacterial growth. In addition, the process scheme of the present invention maintains the broad spectrum bacteriostatic effect of the composition and substantially reduces the color of the product; the product is stable and suitable for use as a preservative in the cosmetic.

EXAMPLE 6

1. Formula

| | |
|---|---|
| Natural antimicrobial agent of Example 1 | 1% |
| *Camellia* seed oil | 8% |
| C16-18 Alcohols | 2% |
| A-165 Emulsifier | 1.5% |
| AVC (acryloyl dimethyl taurine/vinyl pyrrolidone (VP) copolymer | 0.2% |
| Glycerol | 5% |
| Collagen | 2% |
| Oat-β-glucan (content 1%) | 5% |
| Ethylenediamine tetraacetic acid disodium | 0.02% |
| Water | Make up to 100% (to 100 g) |

2. Preparation Process
(1) Add water, glycerol and ethylenediamine tetraacetic acid disodium to the reactor; heat to 85° C.; stir at a speed of 300 rpm/min; slowly add AVC. This was the aqueous phase.
(2) Add A-165, C16-18 alcohols, *camellia* seed oil into the reactor; heat to 85° C.; stir at a speed of 300 rpm/min. This was the oil phase.
(3) Add the oil phase of step (2) to the aqueous phase of step (1); homogenize (speed 500 rpm/min) for 5 min; stir and cool to 45° C.
(4) Add the natural antimicrobial agent of Example 1, collagen and oat-β-glucan to the cooled system of step (3); stir (speed 500 rpm/min) and cool to room temperature to obtain the cosmetic.

EXAMPLE 7

1. Formula

| | |
|---|---|
| Natural antimicrobial agent of Example 2 | 1% |
| *Camellia* seed oil | 8% |
| C16-18 Alcohols | 2% |
| A-165 Emulsifier | 1.5% |
| AVC (acryloyl dimethyl taurine/vinyl pyrrolidone (VP) copolymer | 0.2% |
| Glycerol | 5% |
| Collagen | 2% |
| Oat-β-glucan (content 1%) | 5% |
| Ethylenediamine tetraacetic acid disodium | 0.02% |
| Water | Make up to 100% (to 100 g) |

2. Preparation Process
(1) Add water, glycerol and ethylenediamine tetraacetic acid disodium to the reactor; heat to 85° C.; stir at a speed of 300 rpm/min; slowly add AVC. This was the aqueous phase.
(2) Add A-165, C16-18 alcohols, *camellia* seed oil into the reactor; heat to 85° C.; stir at a speed of 300 rpm/min. This was the oil phase.
(3) Add the oil phase of step (2) to the aqueous phase of step (1); homogenize (speed 500 rpm/min) for 5 min; stir and cool to 45° C.

(4) Add the natural antimicrobial agent of Example 2, collagen and oat-β-glucan to the cooled system of step (3); stir (speed 500 rpm/min) and cool to room temperature to obtain the cosmetic.

EXAMPLE 8

1. Formula

| | |
|---|---|
| Natural antimicrobial agent of Example 1 | 0.5% |
| 1,2-octanediol | 0.2% |
| Camellia seed oil | 8% |
| C16-18 Alcohols | 2% |
| A-165 Emulsifier | 1.5% |
| AVC (acryloyl dimethyl taurine/vinyl pyrrolidone (VP) copolymer | 0.2% |
| Glycerol | 5% |
| Collagen | 2% |
| Oat-β-glucan (content 1%) | 5% |
| Ethylenediamine tetraacetic acid disodium | 0.02% |
| Water | Make up to 100% (to 100 g) |

2. Preparation Process
(1) Add water, glycerol and ethylenediamine tetraacetic acid disodium to the reactor; heat to 85° C.; stir at a speed of 300 rpm/min; slowly add AVC. This was the aqueous phase.
(2) Add A-165, C16-18 alcohols, camellia seed oil into the reactor; heat to 85° C.; stir at a speed of 300 rpm/min. This was the oil phase.
(3) Add the oil phase of step (2) to the aqueous phase of step (1); homogenize (speed 500 rpm/min) for 5 min; stir and cool to 45° C.
(4) Add the natural antimicrobial agent of Example 1, 1,2-octanediol, collagen and oat-β-glucan to the cooled system of step (3); stir (speed 500 rpm/min) and cool to room temperature to obtain the cosmetic.

COMPARATIVE EXAMPLE 4

1. Formula

| | |
|---|---|
| Natural antimicrobial agent of Comparative Example 1 | 0.5% |
| Camellia seed oil | 8% |
| C16-18 Alcohols | 2% |
| A-165 Emulsifier | 1.5% |
| AVC(acryloyl dimethyl taurine/vinyl pyrrolidone (VP) copolymer | 0.2% |
| Glycerol | 5% |
| Collagen | 2% |
| Oat-β-glucan (content 1%) | 5% |
| Ethylenediamine tetraacetic acid disodium | 0.02% |
| Water | Make up to 100% (to 100 g) |

2. Preparation Process
(1) Add water, glycerol and ethylenediamine tetraacetic acid disodium to the reactor; heat to 85° C.; stir at a speed of 300 rpm/min; slowly add AVC. This was the aqueous phase.
(2) Add A-165, C16-18 alcohols, camellia seed oil into the reactor; heat to 85° C.; stir at a speed of 300 rpm/min. This was the oil phase.
(3) Add the oil phase of step (2) to the aqueous phase of step (1); homogenize (speed 500 rpm/min) for 5 min; stir and cool to 45° C.
(4) Add the natural antimicrobial agent of Example 1, collagen and oat-β-glucan to the cooled system of step (3); stir (speed 500 rpm/min) and cool to room temperature to obtain the cosmetic.

COMPARATIVE EXAMPLE 5

1. Formula

| | |
|---|---|
| 1,2-octanediol | 0.2% |
| Camellia seed oil | 8% |
| C16-18 Alcohols | 2% |
| A-165 Emulsifier | 1.5% |
| AVC (acryloyl dimethyl taurine/vinyl pyrrolidone (VP) copolymer | 0.2% |
| Glycerol | 5% |
| Collagen | 2% |
| Oat-β-glucan (content 1%) | 5% |
| Ethylenediamine tetraacetic acid disodium | 0.02% |
| Water | Make up to 100% (to 100 g) |

2. Preparation Process
(1) Add water, glycerol and ethylenediamine tetraacetic acid disodium to the reactor; heat to 85° C.; stir at a speed of 300 rpm/min; slowly add AVC. This was the aqueous phase.
(2) Add A-165, C16-18 alcohols, camellia seed oil into the reactor; heat to 85° C.; stir at a speed of 300 rpm/min. This was the oil phase.
(3) Add the oil phase of step (2) to the aqueous phase of step (1); homogenize (speed 500 rpm/min) for 5 min; stir and cool to 45° C.
(4) Add 1,2-octanediol, collagen and oat-β-glucan to the cooled system of step (3); stir (speed 500 rpm/min) and cool to room temperature to obtain the cosmetic.

EXAMPLE 9

1. Formula

| | |
|---|---|
| Natural antimicrobial agent of Example 4 | 1% |
| Camellia seed oil | 8% |
| C16-18 Alcohols | 2% |
| A-165 Emulsifier | 1.5% |
| AVC (acryloyl dimethyl taurine/vinyl pyrrolidone (VP) copolymer | 0.2% |
| Glycerol | 5% |
| Collagen | 2% |
| Oat-β-glucan (content 1%) | 5% |
| Ethylenediamine tetraacetic acid disodium | 0.02% |
| Water | Make up to 100% (to 100 g) |

2. Preparation Process
(1) Add water, glycerol and ethylenediamine tetraacetic acid disodium to the reactor; heat to 85° C.; stir at a speed of 300 rpm/min; slowly add AVC. This was the aqueous phase.
(2) Add A-165, C16-18 alcohols, camellia seed oil into the reactor; heat to 85° C.; stir at a speed of 300 rpm/min. This was the oil phase.
(3) Add the oil phase of step (2) to the aqueous phase of step (1); homogenize (speed 500 rpm/min) for 5 min; stir and cool to 45° C.
(4) Add the natural antimicrobial agent of Example 4, collagen and oat-β-glucan to the cooled system of step (3); stir (speed 500 rpm/min) and cool to room temperature to obtain the cosmetic.

EXAMPLE 10

Anti-corrosion Challenge Test

1. Means and Quantity of Inoculation for Anti-corrosion Challenge Test

Mixed bacteria were used for inoculation. *Staphylococcus aureus, Escherichia coli* and *Pseudomonas aeruginosa* were inoculated into test samples until the bacterial concentration was $10^5$-$10^6$ CFU/g or $10^5$-$10^6$ CFU/mL; as to *Candida albicans* and *Aspergillus niger*, the concentration was $10^4$ CFU/g or $10^4$ CFU/mL. Each was done in triplicates and saline was used as blank control.

2. Separation Detection of Anti-corrosion Challenge

The samples after inoculation were separated and detected at a specific time: 0 h, 48 h, 7 d, 14 d, 21 d and 28 d. After sampling, according to the needs of the experiment, samples were diluted with saline. 100 μL diluted samples was spreaded on TSB and SDB medium plates. Colonies were counted after culture at 28° C.±1° C. or 36° C.±1° C.

3. Criteria for Judging

If the bacteria decreased by 99.9% at day 7, and *Aspergillus niger* and *Candida albicans* decreased by 90%, respectively, and continued to decline within 28 days, which means samples pass the anti-corrosion challenge test.

If the average of any one of the three parallel trials of the mixed bacteria was reduced to 100 CFU/g (CFU/mL) or less at day 7, and all decreased to 0 CFU/g (CFU/mL) or <10 CFU/g (CFU/mL) in 28 days, then the anti-corrosion effect was considered excellent. Anticorrosive challenge results were shown in Tables 2 to 7, and Table 2 to Table 7 were the results of 0 h, 48 h, 7 d, 14 d, 21 d and 28 d anticorrosive challenges.

In the anti-corrosion challenge tests of four applicative examples (Example 6-9) and comparative examples (comparative example 4 and 5), four applicative examples have a bacterial concentration of less than 10 CFU/g at day 7 for *Staphylococcus aureus, Escherichia coli, Pseudomonas aeruginosa, Candida albicans* and *Aspergillus niger*, and the bacterial concentration was still less than 10 CFU/g at day 28, indicating that these four samples showed excellent performance on the anti-corrosion challenge for *Staphylococcus aureus, Escherichia coli, Pseudomonas aeruginosa, Candida albicans* and *Aspergillus niger*.

TABLE 2

Results of 0 h anti-corrosion challenge

| | Strains | | | | |
| --- | --- | --- | --- | --- | --- |
| | Staphylococcus aureus (CFU/g) | Escherichia coli (CFU/g) | Pseudomonas aeruginosa (CFU/g) | Candida albicans (CFU/g) | Aspergillus niger (CFU/g) |
| Example 6 | $1.0 \times 10^5$ | <10000 | <10000 | <100 | $1.5 \times 10^4$ |
| Example 7 | $1.6 \times 10^5$ | <10000 | <10000 | <100 | $2.1 \times 10^4$ |
| Example 8 | $1.4 \times 10^5$ | <10000 | <10000 | <100 | $2.8 \times 10^4$ |
| Comparative example 4 | $1.0 \times 10^5$ | <10000 | <10000 | <10000 | $1.5 \times 10^4$ |
| Comparative example 5 | $1.6 \times 10^5$ | <10000 | <10000 | <10000 | $2.1 \times 10^4$ |
| Comparative example 9 | $2.6 \times 10^5$ | <10000 | <10000 | <100 | $2.8 \times 10^4$ |
| Blank control | $3.4 \times 10^6$ | $1.4 \times 10^6$ | $1.3 \times 10^6$ | $3.6 \times 10^4$ | $3.8 \times 10^4$ |

TABLE 3

Results of 48 h anti-corrosion challenge

| | Strains | | | | |
| --- | --- | --- | --- | --- | --- |
| | Staphylococcus aureus (CFU/g) | Escherichia coli (CFU/g) | Pseudomonas aeruginosa (CFU/g) | Candida albicans (CFU/g) | Aspergillus niger (CFU/g) |
| Example 6 | <100 | <100 | <100 | <10 | <100 |
| Example 7 | <100 | <100 | <100 | <10 | <100 |
| Example 8 | <100 | <100 | <100 | <10 | <100 |
| Comparative example 4 | <1000 | <1000 | <10000 | <10000 | <1000 |
| Comparative example 5 | <10000 | <10000 | <10000 | <1000 | <1000 |
| Comparative example 9 | <100 | <100 | <100 | <10 | <100 |
| Blank control | $6.0 \times 10^6$ | $7.5 \times 10^6$ | $3.5 \times 10^6$ | $4.0 \times 10^4$ | $3.9 \times 10^4$ |

TABLE 4

Results of 7 d anti-corrosion challenge

| | Strains | | | | |
| --- | --- | --- | --- | --- | --- |
| | Staphylococcus aureus (CFU/g) | Escherichia coli (CFU/g) | Pseudomonas aeruginosa (CFU/g) | Candida albicans (CFU/g) | Aspergillus niger (CFU/g) |
| Example 6 | <10 | <10 | <10 | <10 | <10 |
| Example 7 | <10 | <10 | <10 | <10 | <10 |
| Example 8 | <10 | <10 | <10 | <10 | <10 |
| Comparative example 4 | <100 | <100 | <1000 | <1000 | <100 |
| Comparative example 5 | <10000 | <10000 | <10000 | <100 | <100 |
| Comparative example 9 | <10 | <10 | <10 | <10 | <10 |
| Blank control | $6.0 \times 10^6$ | $6.5 \times 10^6$ | $4.2 \times 10^6$ | $2.8 \times 10^4$ | $2.9 \times 10^4$ |

TABLE 5

Results of 14 d anti-corrosion challenge

| | Strains | | | | |
| --- | --- | --- | --- | --- | --- |
| | Staphylococcus aureus (CFU/g) | Escherichia coli (CFU/g) | Pseudomonas aeruginosa (CFU/g) | Candida albicans (CFU/g) | Aspergillus niger (CFU/g) |
| Example 6 | <10 | <10 | <10 | <10 | <10 |
| Example 7 | <10 | <10 | <10 | <10 | <10 |
| Example 8 | <10 | <10 | <10 | <10 | <10 |
| Comparative example 4 | <10 | <10 | <100 | <100 | <10 |
| Comparative example 5 | <1000 | <1000 | <1000 | <10 | <10 |
| Comparative example 9 | <10 | <10 | <10 | <10 | <10 |
| Blank control | $6.3 \times 10^6$ | $7.3 \times 10^6$ | $6.5 \times 10^6$ | $3.0 \times 10^4$ | $3.5 \times 10^4$ |

TABLE 6

Results of 21 d anti-corrosion challenge

| | Strains | | | | |
|---|---|---|---|---|---|
| | Staphylococcus aureus (CFU/g) | Escherichia coli (CFU/g) | Pseudomonas aeruginosa (CFU/g) | Candida albicans (CFU/g) | Aspergillus niger (CFU/g) |
| Example 6 | <10 | <10 | <10 | <10 | <10 |
| Example 7 | <10 | <10 | <10 | <10 | <10 |
| Example 8 | <10 | <10 | <10 | <10 | <10 |
| Comparative example 4 | <10 | <10 | <1000 | <1000 | <10 |
| Comparative example 5 | <1000 | <1000 | <1000 | <10 | <10 |
| Comparative example 9 | <10 | <10 | <10 | <10 | <10 |
| Blank control | $5.8 \times 10^6$ | $7.5 \times 10^6$ | $7.5 \times 10^6$ | $4.0 \times 10^4$ | $3.3 \times 10^4$ |

TABLE 7

Results of 28 d anti-corrosion challenge

| | Strains | | | | |
|---|---|---|---|---|---|
| | Staphylococcus aureus (CFU/g) | Escherichia coli (CFU/g) | Pseudomonas aeruginosa (CFU/g) | Candida albicans (CFU/g) | Aspergillus niger (CFU/g) |
| Example 6 | <10 | <10 | <10 | <10 | <10 |
| Example 7 | <10 | <10 | <10 | <10 | <10 |
| Example 8 | <10 | <10 | <10 | <10 | <10 |
| Comparative example 4 | <10 | <10 | <1000 | <1000 | <10 |
| Comparative example 5 | <1000 | <1000 | <1000 | <10 | <10 |
| Comparative example 9 | <10 | <10 | <10 | <10 | <10 |
| Blank control | $4.9 \times 10^6$ | $6.3 \times 10^6$ | $5.8 \times 10^6$ | $4.3 \times 10^4$ | $3.1 \times 10^4$ |

EXAMPLE 11

Repeated Skin Irritation Test

1. Method of exposure: 16 ordinary New Zealand rabbits were divided into four groups, each group of four, male and female half. Before the test, the experimental animals were sheared on both sides of the back of the spine (an area about 3 cm×3 cm on left and right sides). Approximately 0.5 g of the test sample was applied to the skin on the left side of the animal, smear area of about 2.5 cm/2.5 cm, the other side as a blank control. Animals were smeared once a day for a continuous 14 days. From the next day, animals were sheared each time before the application of test samples. The residual test samples were removed with pure water. The control area was under the same treatment. Results were observed after one hour.
2. Observation of the results: Skin responses were observed under natural light and scored on skin erythema and edema according to Table 8 (Criteria for skin irritation score) for 14 days.
3. Determination of results: The average score of each animal on each day was calculated according to the following formula, and the stimulus intensity was evaluated.

The average score of each animal on each day=
($\Sigma$erythema and edema/test animal)/14

TABLE 8

Criteria for skin irritation reactions score

| Irritation reactions | Score |
|---|---|
| Formation of erythema and eschar | |
| No erythema | 0 |
| Mild erythema (barely visible) | 1 |
| Obvious erythema | 2 |
| Moderate-severe erythema | 3 |
| Severe erythema (purplish red) to mild edema formation | 4 |
| Edema formation | |
| No edema | 0 |
| Mild edema (barely visible) | 1 |
| Mild edema (the outline of uplift skin is clear) | 2 |
| Moderate edema (skin uplifts 1 mm) | 3 |
| Severe edema (skin uplifts over 1 mm and scope expands | 4 |
| Highest score | 8 |

4. The test results for each group of samples were shown in Tables 9-12.

TABLE 9

Example 6 multiple skin irritation test results for New Zealand rabbits

| | | Scores of skin irritation reaction | | | | | |
|---|---|---|---|---|---|---|---|
| | | Samples | | | Controls | | |
| Applying days | Animal numbers | Erythema | Edema | Total score | Erythema | Edema | Total score |
| 1 | 4 | 1 | 0 | 1 | 0 | 0 | 0 |
| 2 | 4 | 2 | 0 | 2 | 0 | 0 | 0 |
| 3 | 4 | 1 | 0 | 1 | 0 | 0 | 0 |
| 4 | 4 | 2 | 0 | 2 | 0 | 0 | 0 |
| 5 | 4 | 2 | 0 | 2 | 0 | 0 | 0 |
| 6 | 4 | 1 | 0 | 1 | 0 | 0 | 0 |
| 7 | 4 | 2 | 0 | 2 | 0 | 0 | 0 |
| 8 | 4 | 2 | 0 | 2 | 0 | 0 | 0 |
| 9 | 4 | 3 | 0 | 3 | 0 | 0 | 0 |
| 10 | 4 | 1 | 0 | 1 | 0 | 0 | 0 |
| 11 | 4 | 2 | 0 | 2 | 0 | 0 | 0 |
| 12 | 4 | 2 | 0 | 2 | 0 | 0 | 0 |
| 13 | 4 | 1 | 0 | 1 | 0 | 0 | 0 |
| 14 | 4 | 1 | 0 | 1 | 0 | 0 | 0 |
| The average score of each animal for 14 days | | Sample group: 5.75 | | | Control group: 0 | | |
| The daily average score of each animal | | Sample group: 0.41 | | | Control group: 0 | | |

Results showed that the skin irritation of New Zealand rabbits subjected from the test samples was light irritation.

TABLE 10

Example 7 multiple skin irritation test results for New Zealand rabbits

| | | Scores of skin irritation reaction | | | | | |
|---|---|---|---|---|---|---|---|
| | | Samples | | | Controls | | |
| Applying days | Animal numbers | Erythema | Edema | Total score | Erythema | Edema | Total score |
| 1 | 4 | 1 | 0 | 3 | 0 | 0 | 0 |
| 2 | 4 | 1 | 0 | 3 | 0 | 0 | 0 |
| 3 | 4 | 1 | 0 | 3 | 0 | 0 | 0 |
| 4 | 4 | 2 | 0 | 4 | 0 | 0 | 0 |
| 5 | 4 | 2 | 0 | 5 | 0 | 0 | 0 |
| 6 | 4 | 1 | 0 | 7 | 0 | 0 | 0 |
| 7 | 4 | 2 | 0 | 3 | 0 | 0 | 0 |
| 8 | 4 | 1 | 0 | 4 | 0 | 0 | 0 |
| 9 | 4 | 1 | 0 | 4 | 0 | 0 | 0 |
| 10 | 4 | 1 | 0 | 4 | 0 | 0 | 0 |
| 11 | 4 | 2 | 0 | 3 | 0 | 0 | 0 |
| 12 | 4 | 2 | 0 | 3 | 0 | 0 | 0 |
| 13 | 4 | 1 | 0 | 3 | 0 | 0 | 0 |
| 14 | 4 | 3 | 0 | 3 | 0 | 0 | 0 |
| The average score of each animal for 14 days | | Sample group: 5.25 | | | Control group: 0 | | |
| The daily average score of each animal | | Sample group: 0.375 | | | Control group: 0 | | |

Results showed that the skin irritation of New Zealand rabbits subjected from the test samples was light irritation.

TABLE 11

Example 8 multiple skin irritation test results for New Zealand rabbits

| | | Scores of skin irritation reaction | | | | | |
|---|---|---|---|---|---|---|---|
| | | Samples | | | Samples | | |
| Applying days | Animal numbers | Erythema | Edema | Total score | Erythema | Edema | Total score |
| 1 | 4 | 3 | 0 | 3 | 0 | 0 | 0 |
| 2 | 4 | 3 | 0 | 3 | 0 | 0 | 0 |
| 3 | 4 | 3 | 0 | 3 | 0 | 0 | 0 |
| 4 | 4 | 2 | 0 | 3 | 0 | 0 | 0 |
| 5 | 4 | 2 | 0 | 3 | 0 | 0 | 0 |
| 6 | 4 | 3 | 0 | 3 | 0 | 0 | 0 |
| 7 | 4 | 4 | 0 | 4 | 0 | 0 | 0 |
| 8 | 4 | 4 | 0 | 4 | 0 | 0 | 0 |
| 9 | 4 | 4 | 0 | 4 | 0 | 0 | 0 |
| 10 | 4 | 4 | 0 | 4 | 0 | 0 | 0 |
| 11 | 4 | 3 | 0 | 3 | 0 | 0 | 0 |
| 12 | 4 | 3 | 0 | 3 | 0 | 0 | 0 |
| 13 | 4 | 3 | 0 | 3 | 0 | 0 | 0 |
| 14 | 4 | 3 | 0 | 3 | 0 | 0 | 0 |
| The average score of each animal for 14 days | | Sample group: 11 | | | Control group: 0 | | |
| The daily average score of each animal | | Sample group: 0.78 | | | Control group: 0 | | |

Results showed that the skin irritation of New Zealand rabbits subjected from the test samples was light irritation.

TABLE 12

Example 9 multiple skin irritation test results for New Zealand rabbits

| | | Scores of skin irritation reaction | | | | | |
|---|---|---|---|---|---|---|---|
| | | Samples | | | Samples | | |
| Applying days | Animal numbers | Erythema | Edema | Total score | Erythema | Edema | Total score |
| 1 | 4 | 3 | 0 | 3 | 0 | 0 | 0 |
| 2 | 4 | 5 | 0 | 5 | 0 | 0 | 0 |
| 3 | 4 | 3 | 0 | 3 | 0 | 0 | 0 |
| 4 | 4 | 6 | 0 | 6 | 0 | 0 | 0 |
| 5 | 4 | 5 | 0 | 5 | 0 | 0 | 0 |
| 6 | 4 | 6 | 0 | 6 | 0 | 0 | 0 |
| 7 | 4 | 4 | 0 | 4 | 0 | 0 | 0 |
| 8 | 4 | 4 | 0 | 4 | 0 | 0 | 0 |
| 9 | 4 | 5 | 0 | 5 | 0 | 0 | 0 |
| 10 | 4 | 4 | 0 | 4 | 0 | 0 | 0 |
| 11 | 4 | 3 | 0 | 3 | 0 | 0 | 0 |
| 12 | 4 | 4 | 0 | 4 | 0 | 0 | 0 |
| 13 | 4 | 5 | 0 | 5 | 0 | 0 | 0 |
| 14 | 4 | 3 | 0 | 3 | 0 | 0 | 0 |
| The average score of each animal for 14 days | | Sample group: 15 | | | Control group: 0 | | |
| The daily average score of each animal | | Sample group: 1.07 | | | Control group: 0 | | |

Results showed that the skin irritation of New Zealand rabbits subjected from the test samples was light irritation.

From the comparison of the four examples (Examples 6 to 9) of the application, it can be seen that the natural antimicrobial agent prepared under the enzymatic process was much less irritating than the antibacterial agent prepared under no enzymatic conditions, indicating that enzymolysis can greatly reduce the irritation of antimicrobial agents.

EXAMPLE 12

Human Skin Patch Test

1. Patch test method: Approximately 0.020 g-0.025 g of the test sample was applied to qualified patch test device in a closed patch test method and then applied to the forearm side of the subject with an external use tape. After 24 hours, the test sample was removed and the skin reaction was observed 30 min after the removal of the test sample and the indentation disappeared. The results were recorded according to the skin reaction grouping criteria of "Cosmetic Hygiene Standard" (2007 edition).

2. Results evaluation: The results of the human skin patch test of Examples 6 to 9 were shown in Table 14 according to the grouping criteria in Table 13 (skin adverse reaction grouping criteria).

TABLE 13

Skin adverse reaction grouping criteria

| The degree of reaction | Score level | Skin reactions |
|---|---|---|
| − | 0 | Negative reaction |
| ± | 1 | Suspicious reaction; only slight erythema |
| + | 2 | Weak positive reaction (erythema recation); erythema, infiltration, edema, may have pimples |
| ++ | 3 | Strong positive reaction (herpes response); erythema, infiltration, edema, pimples, herpes; reaction can be beyond the test area |

TABLE 13-continued

Skin adverse reaction grouping criteria

| The degree of reaction | Score level | Skin reactions |
|---|---|---|
| +++ | 4 | Very strong positive response (fusion herpes response); obvious erythema, severe infiltration, edema, fusion herpes; reaction beyond the test area |

TABLE 14

The results of the human skin patch test of Examples 6 to 9

| | Number of subjects | Time point | Number of different skin reactions in patch test | | | | |
|---|---|---|---|---|---|---|---|
| | | | 0 grade | 1 grade | 2 grade | 3 grade | 4 grade |
| Example 6 | 30 | 24 h | 30 | 0 | 0 | 0 | 0 |
| Example 7 | 30 | 24 h | 30 | 0 | 0 | 0 | 0 |
| Example 8 | 30 | 24 h | 30 | 0 | 0 | 0 | 0 |
| Example 9 | 30 | 24 h | 25 | 5 | 0 | 0 | 0 |
| Control | 30 | 24 h | 30 | 0 | 0 | 0 | 0 |

The results of human skin patch test of each group in table 14 showed that 30 subjects have negative reactions in Examples 6 to 8, whereas in Example 9, 5 cases were suspicious, with only weak erythema (rating: 0 level). The samples obtained in Examples 6 to 8 had no skin adverse effects on the human body according to the criteria for judging the human skin patch test in "Cosmetics Hygienic Standard" (2007 edition). The sample obtained in Example 9 was a suspicious reaction, further indicating the significance of enzymolysis in the present invention.

The foregoing is only a preferred embodiment of the present invention and it should be noted that several improvements and modifications may be made by those of ordinary skill in the art without departing from the principles of the invention, which should be regarded as within the scope of the present invention.

The invention claimed is:

1. An antimicrobial traditional Chinese medicine composition, which is made from materials comprising Perillae Fructus, Pogostemonis Herba and Usnea, wherein in parts by weight, said materials comprise 60-80 parts of Perillae Fructus, 10-20 parts of Pogostemonis Herba and A parts of Usnea, $0 < A \leq 20$.

2. The antimicrobial traditional Chinese medicine composition according to claim 1, wherein in parts by weight, said materials comprise 60 parts of Perillae Fructus, 20 parts of Pogostemonis Herba and 20 parts of Usnea.

3. The antimicrobial traditional Chinese medicine composition according to claim 1, wherein in parts by weight, said materials comprise 80 parts of Perillae Fructus, 10 parts of Pogostemonis Herba and 10 parts of Usnea.

4. The antimicrobial traditional Chinese medicine composition according to claim 1, wherein in parts by weight, said materials comprise 70 parts of Perillae Fructus, 15 parts of Pogostemonis Herba and 15 parts of Usnea.

5. A method for preparing the antimicrobial traditional Chinese medicine composition according to claim 1, comprising the following steps: mixing Perillae Fructus, Pogostemonis Herba and Usnea, wherein the weight of Perillae Fructus is 60-80 parts, the weight of Pogostemonis Herba is 10-20 parts, the weight of Usnea is A parts, $0 < A \leq 20$; and performing ethanol percolation extraction to obtain the antimicrobial traditional Chinese medicine composition.

6. The method according to claim 5, also comprising enzymolysis by using lipases after mix and before extraction.

7. The method according to claim 5, wherein said mix comprises:

mixing Perillae Fructus, Pogostemonis Herba and Usnea;
adding water and grinding until 60-200 mesh; and
adjusting pH to 4-7.

8. The method according to claim 7, wherein the extraction time is 24 h-30 h, and after extraction, the method also comprises:

filtering and collecting filtered solution; and
the filtered solution is subjected to concentration, constant volume and aging, successively, to obtain the antimicrobial traditional Chinese medicine composition.

9. A method for corrosion prevention in pharmaceuticals, cosmetics or foods comprising administering to the pharmaceuticals, cosmetics or foods the antimicrobial traditional Chinese medicine composition according to claim 1.

* * * * *